(12) United States Patent
Izmailov et al.

(10) Patent No.: US 7,720,612 B2
(45) Date of Patent: May 18, 2010

(54) METHODS FOR RESOLVING CONVOLUTED PEAKS IN A CHROMATOGRAM

(75) Inventors: Alexandre M. Izmailov, Etobicoke (CA); Murugathas Yuwaraj, Markham (CA)

(73) Assignee: Siemens Healthcare Diagnostics, Inc., Tarrytown, NY (US)

(*) Notice: Subject to any disclaimer, the term of this patent is extended or adjusted under 35 U.S.C. 154(b) by 0 days.

(21) Appl. No.: 12/159,213

(22) PCT Filed: Feb. 6, 2007

(86) PCT No.: PCT/US2007/061706
§ 371 (c)(1),
(2), (4) Date: Jun. 26, 2008

(87) PCT Pub. No.: WO2007/092855
PCT Pub. Date: Aug. 16, 2007

(65) Prior Publication Data
US 2008/0306696 A1  Dec. 11, 2008

Related U.S. Application Data

(60) Provisional application No. 60/765,506, filed on Feb. 6, 2006.

(51) Int. Cl.
*G01N 31/00* (2006.01)
*G01N 33/48* (2006.01)

(52) U.S. Cl. .............................. 702/19; 702/28; 702/32
(58) Field of Classification Search .................. 702/19, 702/22, 28, 30, 32; 356/344; 435/6; 436/164
See application file for complete search history.

(56) References Cited

U.S. PATENT DOCUMENTS

| | | | |
|---|---|---|---|
| 4,807,148 A | 2/1989 | Lacey | |
| 5,121,337 A | 6/1992 | Brown | |
| 5,567,625 A | 10/1996 | Kurtzberg et al. | |
| 2002/0147548 A1 | 10/2002 | Walther et al. | |
| 2007/0233392 A1* | 10/2007 | Jojic et al. | .......... 702/19 |

FOREIGN PATENT DOCUMENTS

WO  2006067648  12/2006

* cited by examiner

*Primary Examiner*—John H Le

(57) ABSTRACT

The present invention relates to methods for resolving convoluted peaks in a chromatogram into one or more constituent peaks using peak resolution values. The peaks methods of the invention determine empirical peak resolution values of "well-defined" or "isolated" peaks in the data, then extrapolate these empirical resolution values to peaks in neighboring regions to predict the number of constituent peaks at a given peak position. Predicted peak resolution values are compared to observed peak resolution values of low-resolution or convoluted peaks to determine the number of constituent peaks in the convoluted peaks. These methods enable extension of the region of data that can used for identifying nucleotide sequences, and increase base-calling accuracy in the low-resolution region (end region) of data.

31 Claims, 4 Drawing Sheets

Figure 1(a): High resolution region of a typical chromatogram (acquired towards the middle of a sequencing run)

Figure 1(b): Low resolution region of a typical chromatogram (acquired towards the end of a sequencing run)

METHODS FOR RESOLVING CONVOLUTED PEAKS IN A CHROMATOGRAM

CROSS REFERENCE TO RELATED APPLICATION

This application claims the benefit of the filing date of U.S. Provisional Patent Application No. 60/765,506, filed Feb. 6, 2006, and International Application Number PCT/US2007/061707, filed Feb. 6, 2007, the disclosures of which are incorporated, in their entirety, by this reference.

FIELD OF THE INVENTION

The present invention relates generally to the field of analysis of chromatographic signals representing separation patterns of mixtures of molecules, such as nucleic acid sequences.

BACKGROUND OF THE INVENTION

Mixtures of molecular compounds are often separated into their various constituents using chromatographic techniques, based upon their differential migration or movement through a sieving medium according to certain properties, such as molecular weight or affinity for a solid adsorbent. The separated constituent compounds may be visualized by a number of different techniques, most of which require that the constituent compounds be labeled with a molecule that emits electromagnetic radiation, such as a fluorescent dye. This radiation can be detected by an optical detector sensitive in the spectral range of emitted radiation and then converted to an electronic or visual signal indicating the identity, amount, and order of the labeled fragments.

Chromatographic methods are commonly used to determine the sequence of a nucleic acid sample. Such methods involve the electrophoretic separation of mixtures of nucleic acid chain-termination fragments representing a size-distribution of fragments terminating at each A, G, T and C of the nucleic acid, with each fragment being labeled with a detectable label specific to the base type (A, T, G, or C) of the last nucleotide base of the fragment (in the case of dye-terminator labeling chemistry). Alternatively the primer used in the sequencing reaction can be labeled. The chain termination fragments are electrophoretically separated in a gel medium according to the fragment size, resulting in a pattern of bands corresponding to the order of the terminal nucleic acid base type. An optical detector detects the signal emitted by the fragment labels in the order of migration and converts the signal to a visualized pattern of peaks representing discrete constituent terminal nucleotide bases of each fragment. The pattern of peaks can then be analyzed by signal processing technology and/or computer, to determine the order, quantity, and identity of the terminating base type (and hence the sequence) of the individual components nucleic acid sample. Data acquired by an electrophoresis-based instrument, such as a slab-gel or capillary system) is known as a chromatogram or data trace, which provides a chronological series of peaks representing the nucleotide sequence.

Because chromatographic methods of nucleic acid sequencing utilize an electrophoretic sieving medium to separate DNA fragments on the basis of size, the accuracy of the sequence results depends on accurate detection of the chronological order in which the fragments migrate through the medium, as indicated by the presence and order of signal peaks representing individual fragments in an chromatogram or sequence data trace. Failure to identify a peak will result in loss of a base (called deletion error) in the identified sequence where a base actually exists. Identification of a false-positive peak (a peak that does not in fact represent a real nucleotide fragment) will result in a nucleotide/base being inserted (insertion error) in the identified sequence where no base actually exists.

Accurate identification of the order, identity and quantity of constituent components (e.g., nucleic acid base types) of a chromatographic separation process is critical for many applications. However, the accuracy of current methods is limited by a number of factors. First, the spacing of peaks produced by fragments differing in length by a single nucleotide tends to change with size of the fragment. Differences in the spacing of bands among multiple lanes also contributes to inaccuracies. Additionally, the electromagnetic radiation emitted by the detectable label is inherently stochastic in nature, resulting in a spread or dispersion of the signal. Background noise is also inherent, and contributes to a low but variable pattern of visual darkening or visual signal over the lane and in the peaks representing the signal. The general intensity of labeling often varies between the four nucleotide types, and there is furthermore a tendency for bands within a given lane to vary in relative intensity in an unpredictable manner. Consequently, signals generated by the detectable labels of the components are not discrete, and often result in overlapping peaks, which tend to occur frequently towards the end of the sequence, especially when there is a run of multiple components having the same identity (e.g., AAAAA, GGG or CCCC) which become convoluted and appear as a single peak. Overlapping peaks generally occur as a result of the reduction of resolution provided by a sieving medium with the length of the nucleic acid fragment. All of above factors contribute to difficulties in resolving individual constituent peaks, ordering of the peaks, and determining the correct sequence of bases.

Various methods have been utilized to circumvent the above problems and improve the accuracy of base-calling, including highly configurable data processing modules, homomorphic deconvolution followed by peak detection, neural networks, grid search assuming regularly spaced Gaussian pulses, expert systems, and others. The various methods generally fall into two categories: deconvolution methods and peak-fitting methods. Peak-fitting methods are based on empirical knowledge of the number, location, and characteristics of peaks of the same or a cognate sequence. Peak-fitting methods, however, require empirical knowledge of related sequences, and cannot be used where such empirical data is not available. Deconvolution methods, on the other hand, are based on an unbiased interpretation of data inherent in the peak data generated by the sample sequence, and involve an enhancement of the data by means of computational elimination or reduction of variables contributing to the blurring of the peak, which should theoretically result in an ideal discrete profile peak. Typical deconvolution base-calling methods use simple Fourier methods to predict base positions and then find peaks in the data as regions about inflexions or concavities in the signal that exceed certain area thresholds. Deconvolution methods, however, have limited utility where such inflexions between peaks are not present. Deconvolution is also highly sensitive to noise.

Accordingly, there is a continuing need to develop improved methods of base-calling, particularly methods that are capable of resolving peaks in low-resolution regions of peak data.

SUMMARY OF THE INVENTION

The present invention relates to methods for resolving apparent peaks in a sample chromatogram into one or more constituent peaks. Generally, the methods of the present invention empirically determine resolution values of "well-defined" or "isolated" peaks in the data, and then extrapolate the empirical resolution values to low-resolution or convoluted peaks in neighboring regions to predict the actual number of constituent peaks in the data. The methods of the present invention enable extension of the region of data that can be used for identifying nucleotide sequences. In addition, the methods of the invention also increase base-calling accuracy in the low-resolution region (end region) of data, as a result of the use of information derived from the high-resolution (early region) of data.

The methods and systems of the present invention generally include using peak information from well-defined regions of the data to predict peak information for regions of the data that are not well-defined. The process for obtaining peak information from well-defined regions includes detecting well-defined (isolated) peaks, building a mathematical model or representation of peak height, spacing and area, and detecting peaks that satisfy the mathematical model of a well-defined peak. The process for using that known information to predict peak information for regions of the data that are not well-defined includes building a model of peak resolution based upon the information from the well-defined peaks, and resolving overlapping or low-resolution peaks based upon a comparison between the predicted peak resolution values and the observed peak resolution values.

In one aspect, the methods of the present invention comprise the steps of:

(a) selecting a plurality of well-defined peaks in a chromatogram;

(b) calculating an observed peak resolution value, as a function of peak position, of the plurality of well-defined peaks;

(c) extrapolating the observed peak resolution values of the plurality of well-defined peaks in the chromatogram to obtain a predicted peak resolution value, as a function of peak position, of one or more apparent peak in the chromatogram;

(d) calculating an observed peak resolution value, as a function of peak position, of the apparent peaks; and (e) correlating an observed peak resolution value of each apparent peak with a multiple of the predicted peak resolution value of the apparent peak at a corresponding peak position, wherein the multiple represents the number of constituent peaks in the apparent peak.

In another aspect, the present invention is directed to a method for resolving apparent peaks in a sample chromatogram into one or more constituent peaks, wherein the step of selecting a plurality of well-defined peaks in the chromatogram comprises: (a) selecting a first set of well-defined peaks in the chromatogram; (b) generating a model of well-defined peaks, as a function of peak position, for each apparent peak in the chromatogram, based upon the first set of well-defined peaks; (c) selecting a second set of well-defined peaks in the chromatogram that fit the model of well-defined peaks, and wherein the step of calculating an observed peak resolution value, as a function of peak position, of the plurality of well-defined peaks is performed using the second set of well-defined peaks.

In one particular embodiment, the extrapolation is based on the assumption that peak resolution varies gradually.

In another embodiment, the extrapolation is based on an assumption that peak resolution is the ratio of peak spacing to peak width, wherein peak spacing gradually increases from the beginning to the middle of a chromatogram and gradually decreases from the middle to the end of the chromatogram, and peak width gradually increases from the beginning to the end of the chromatogram.

In another embodiment of the invention, the step of correlating an observed peak resolution value of each apparent peak with a multiple of the predicted peak resolution value of the apparent peak at a corresponding peak position comprises calculating, for one or more apparent peak, a ratio of (i) the observed peak resolution value of the apparent peak and (ii) the predicted peak resolution value of the apparent peak at a corresponding peak position, and correlating the value of the ratio with the number of constituent peaks within the apparent peak, thereby resolving the apparent peak into one or more constituent peaks.

In yet another embodiment, the methods include rounding the value of the ratio to the nearest integer, wherein the integer represents an estimate of the number of constituent peaks in the apparent peak.

In still another embodiment, the methods include discarding the apparent peak if the ratio is less than the value of 1.

In another aspect, the present invention relates to a method for generating a model of predicted peak resolution for apparent peaks in a chromatogram, comprising:

(a) selecting a plurality of well-defined peaks in a chromatogram;

(b) calculating an observed peak resolution value, as a function of peak position, of the plurality of well-defined peaks;

(c) extrapolating the observed peak resolution values of the plurality of well-defined peaks in the chromatogram to obtain a predicted peak resolution value, as a function of peak position, of one or more apparent peak in the chromatogram; and (d) calculating an observed peak resolution value, as a function of peak position, of the apparent peaks.

In yet another aspect, the present invention relates to a method for selecting a set of well-defined peaks in a chromatogram, comprising: (a) selecting a first set of well-defined peaks in a chromatogram; (b) generating a model of well-defined peaks comprising one or more values of peak height, peak spacing and peak area, as a function of peak position, based upon the first set of well-defined peaks; and (c) selecting a second set of well-defined peaks in the chromatogram that fit the model of well-defined peaks.

In still another aspect, the present invention relates to a model of peak resolution for peaks of a chromatogram, comprising predicted peak resolution values, as a function of peak position, of a plurality apparent peaks in a chromatogram, wherein the predicted peak resolution values comprise values extrapolated from observed peak resolution values, as a function of peak position, of a plurality of well-defined peaks.

In another aspect, the present invention relates to a set of well-defined peaks of a chromatogram selected by a method comprising: (a) selecting a first set of well-defined peaks in a chromatogram; (b) generating a model of well-defined peaks; and (c) selecting a second set of well-defined peaks in the chromatogram that fit the model of well-defined peaks.

The methods as discussed above may be performed by one or more computer system executing one or more set of computer instructions stored on computer readable medium.

For example, a computer system of one embodiment can be used to generate a model of peak resolution for peaks of a chromatogram, wherein the computer system comprises a memory to store predicted peak resolution values, as a function of peak position, of a plurality of apparent peaks in a chromatogram. The computer system may further comprise a processor to extrapolate values from observed peak resolution values, as a function of peak position, of a plurality of well-defined peaks, the extrapolated values to be incorporated into the stored predicted peak resolution values.

DETAILED DESCRIPTION OF THE INVENTION

Figure 1:
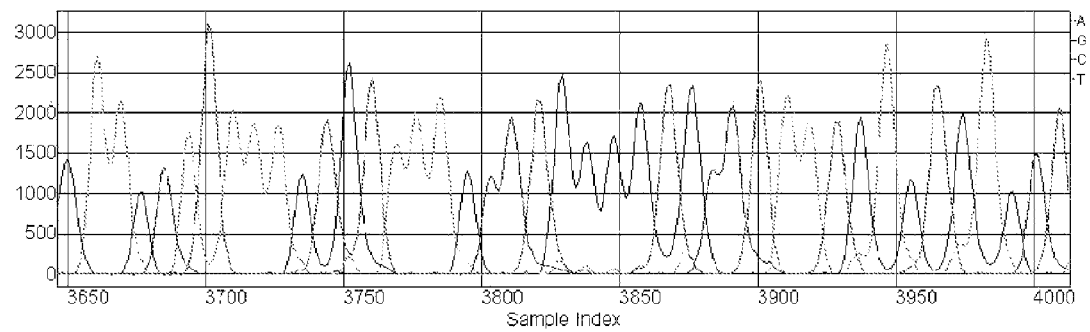
FIG. 1 shows two different portions of a single data trace, one from the early region and one from the end region of a sequencing run, showing that resolution deteriorates towards the end of a sequencing run.
Figure 1:
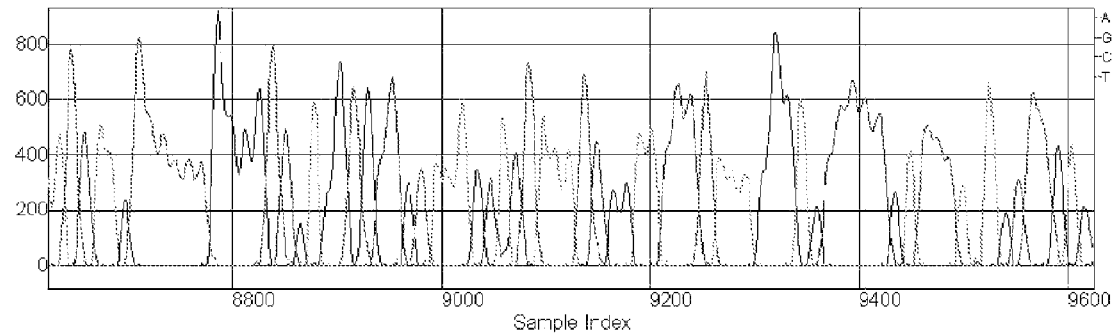
Figure 2:
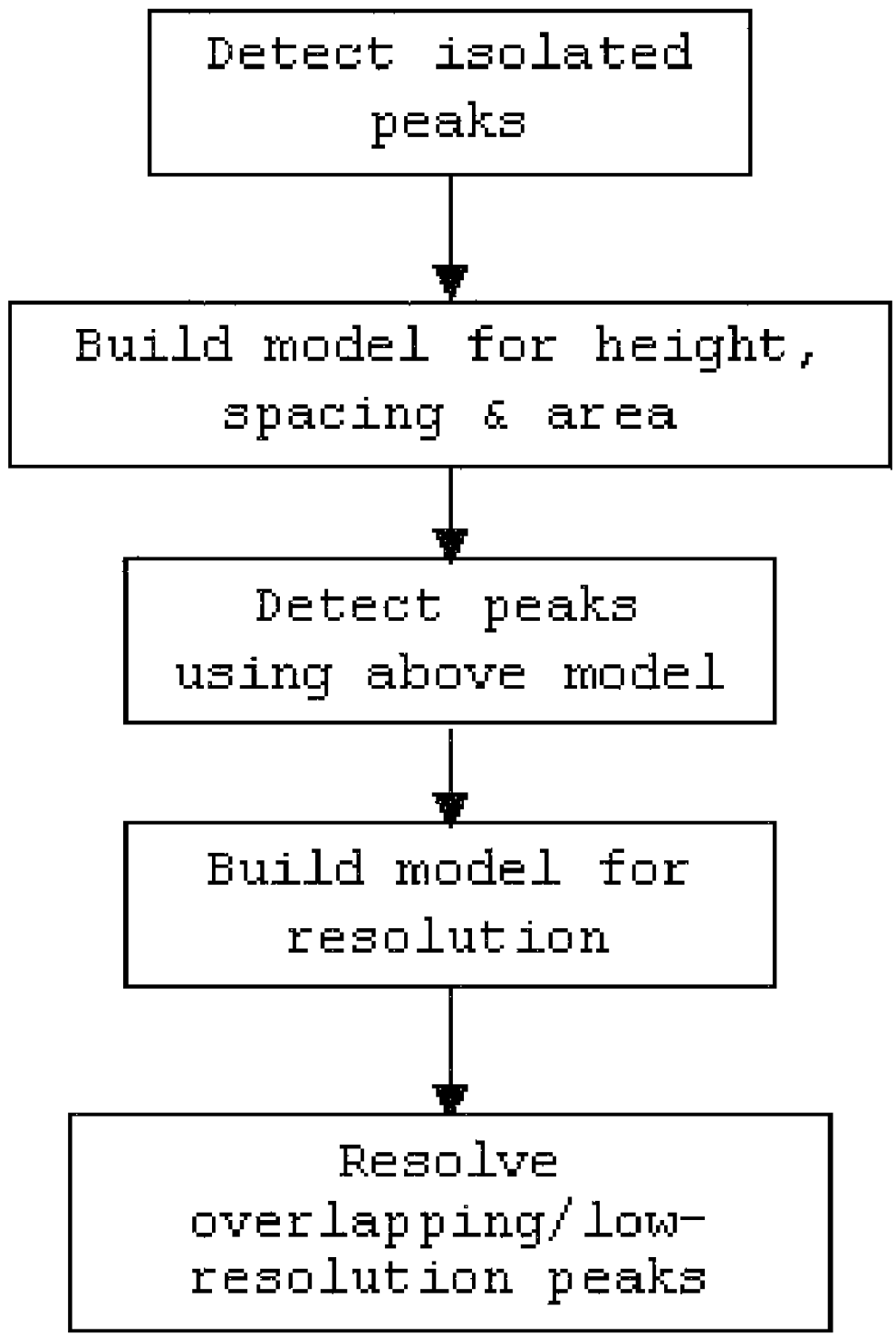
FIG. 2 illustrates the overall steps involved in utilization of a resolution model.
Figure 3:
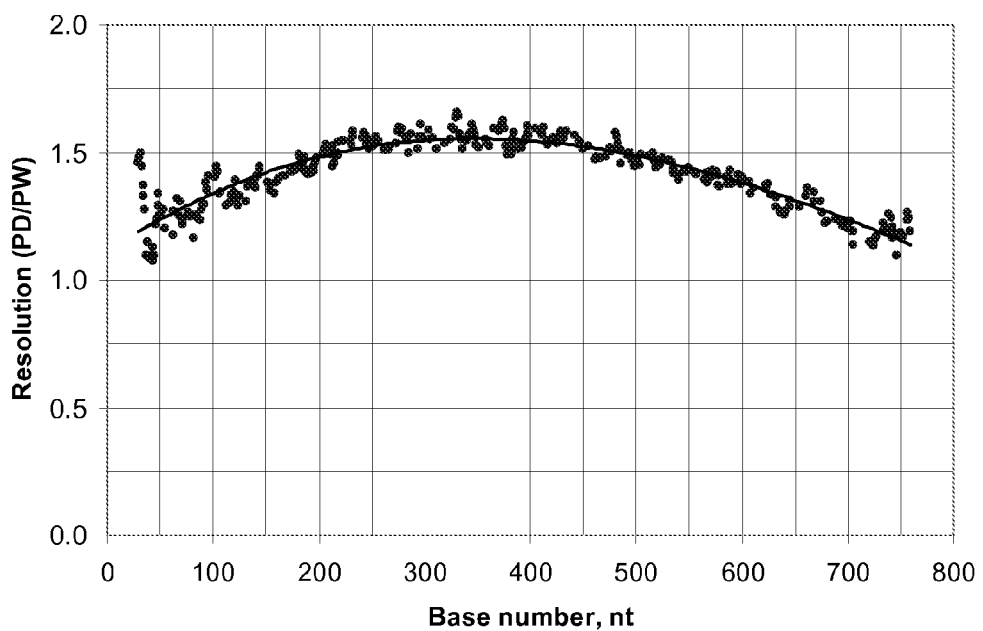
FIG. 3 shows a typical resolution model generated by fitting a polynomial function to the resolution and position values estimated from isolated peaks. Resolution improves towards the middle of a sequencing run and then deteriorates due to both peak broadening (introduced by domination of diffusion effects) and slight increase in inter-peak spacing (introduced by migration properties of DNA fragments under the influence of an electric field).
Figure 4:
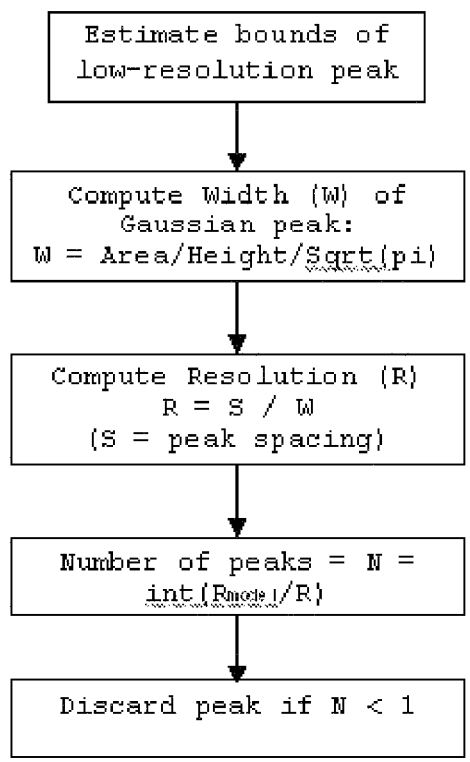
FIG. 4 illustrates the detailed steps necessary to utilize the peak resolution model. Estimated features of a peak are also illustrated in the figure for clarity.
Figure 4:
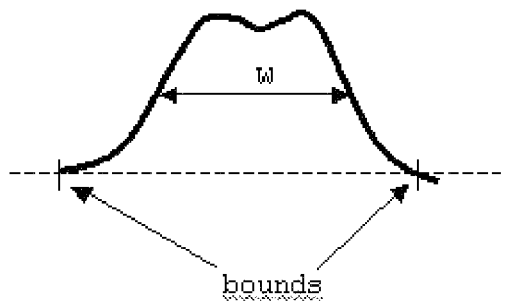

In the following description, numerous specific details of programming, software modules, user options, networks, database queries, database structures, etc., are provided for an understanding of various embodiments of the systems and methods disclosed herein. However, those skilled in the art will recognize that the systems and methods disclosed can be practiced without one or more of the specific details, or with other methods, components, materials, etc.

In some cases, well-known structures, materials, or operations are not shown or described in detail. Furthermore, the described features, structures, or characteristics may be combined in any suitable manner in one or more embodiments. It will also be readily understood that the components of the embodiments could be arranged and designed in a wide variety of different configurations.

The order of the steps or actions of the methods described in connection with the embodiments disclosed may be changed as would be apparent to those skilled in the art. Thus, any order in the figures or detailed description is for illustrative purposes only and is not meant to imply a required order.

Several aspects of the embodiments described may be implemented as software modules or components. As used herein, a software module or component may include any type of computer instruction or computer executable code located within a memory device and/or transmitted as electronic signals over a system bus or wired or wireless network. A software module may, for instance, comprise one or more physical or logical blocks of computer instructions, which may be organized as a routine, program, object, component, data structure, etc., that performs one or more tasks or implements particular abstract data types.

In certain embodiments, a particular software module may comprise disparate instructions stored in different locations of a memory device, which together implement the described functionality of the module. Indeed, a module may comprise a single instruction, or many instructions, and may be distributed over several different code segments, among different programs, and across several memory devices. Some embodiments may be practiced in a distributed computing environment where tasks are performed by a remote processing device linked through a communications network. In a distributed computing environment, software modules may be located in local and/or remote memory storage devices.

Software modules or instructions may be carried out, for instance, on a computer having a processor that communicates with the one or more memory devices listed above having stored thereon the software modules or instructions. The computer may be a personal computer, a server, a laptop, a handheld device, or another processing device known in the art.

DEFINITIONS

While the terminology used in this application is standard within the art, the following definitions of certain terms are provided to assure clarity.

Units, prefixes, and symbols may be denoted in their SI accepted form. Unless otherwise indicated, nucleic acids are written left to right in 5' to 3' orientation. Numeric ranges recited herein are inclusive of the numbers defining the range and include and are supportive of each integer within the defined range. Amino acids may be referred to herein by either their commonly known three letter symbols or by the one-letter symbols recommended by the IUPAC-IUBMB Nomenclature Commission. Nucleotides, likewise, may be referred to by their commonly accepted single-letter codes. Unless otherwise noted, the terms "a" or "an" are to be construed as meaning "at least one of." The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose. In the case of any amino acid or nucleic sequence discrepancy within the application, the figures control.

The term "apparent peak" means an observed peak in a chromatogram. Apparent peaks may constitute either constituent peaks or convoluted peaks.

The term "base-calling" means a computational process of identifying establishing a sequence of nucleotides in the DNA sequence bases on an experimentally recorded chromatogram.

The term "constituent peak" means a peak representing a single component of a mixture of components.

The term "convoluted peak" means a peak that consists of multiple peaks that overlap or are conflated, or that does not otherwise satisfy the criteria of a well-defined peak.

The term "chromatogram" refers to a graphical or numerical representation of a signal, typically in the form of a series of peaks and valleys, representing a chromatographic separation of set of nucleic acid chain termination fragments produced in a chain termination sequencing reaction for a specific nucleic acid sequence and detected in a DNA sequencer. A chromatogram is also sometimes referred to as a "data trace" or "sequence signature." A chromatogram is produced by a system that detects a plurality of discrete molecular entities separated from a mixture into their various constituents by differential migration or movement through a sieving medium on the basis of different physical properties, such as molecular weight or affinity for a solid adsorbent. A chromatogram is generally an array of numbers, typically represented as a plot corresponding to a signal generated by a source of electromagnetic radiation emissions versus time or relative position of components migrating within the mobile phase. In the context of nucleic acid sequencing, a chromatogram is generated as a result of the electrophoretic separation of nucleic acid fragments of different size over time. The chromatogram usually comprises one or more peaks, each peak representing the location of an individual component relative to other components (plotted on the time or molecular weight scale), with the area under the peak providing a quantitative measure of that component (plotted on the signal intensity scale). Although a chromatogram is generally in the form of a graphical representation of peaks and valleys, it is to be understood that a chromatogram may also take the form of a stream (array) of numerical values or, alternatively, a mathematical (i.e., polynomial) expression or function, or a database of values (i.e., peak characteristics, such as peak height, peak width, peak area, etc.) as a function of time or relative position in the order of migration. The chromatogram used in the present invention may be either a raw chromatogram or a conditioned chromatogram.

The term "model" or "profile" means a function in which the values of one variable correspond to the values of another variable. The term "profile" encompasses the correspondence or association of empirically determined values, as well as the correspondence or association of values extrapolated from empirically determined values. A model will generally take the form of a curve fitted to empirically determined data, which curve may be represented graphically, numerically, or mathematically in the form of a polynomial function. In the context of the present invention, a "profile" of multiple peaks represents a consensus value, or alternatively a range of values, for a particular peak characteristic of a peak at a given peak position for one or more polynucleotides. For example, a profile of peak height comprises a value representing peak height at a particular peak position, as determined by the peak height at that position for one or more samples of the same or similar polynucleotide. Preferably, a profile will include the profiles of all peak positions in the polynucleotide. The "profile" may be represented as a single value of peak height, an average value of peak height, a range of values of peak height, etc.

The terms "nucleic acid" and "polynucleotide" are considered to be equivalent and interchangeable, and refer to polymers of nucleic acid bases comprising any of a group of complex compounds composed of purines, pyrimidines, carbohydrates, and phosphoric acid. Nucleic acids are commonly in the form of DNA or RNA. The term "nucleic acid" includes polynucleotides of genomic DNA or RNA, cDNA, semisynthetic, or synthetic origin. Nucleic acids may also substitute standard nucleotide bases with nucleotide isoform analogs, including, but not limited to iso-C and iso-G bases, which may hybridize more or less permissibly than standard bases, and which will preferentially hybridize with complementary isoform analog bases. Many such isoform bases are described, for example, at www.idtdna.com. The nucleotides adenosine, cytosine, guanine and thymine are represented by their one-letter codes A, C, G, and T respectively. In representations of degenerate primers or mixture of different strands having mutations in one or several positions, the symbol R refers to either G or A, the symbol Y refers to either T/U or C, the symbol M refers to either A or C, the symbol K refers to either G or T/U, the symbol S refers to G or C, the symbol W refers to either A or T/U, the symbol B refers to "not A", the symbol D refers to "not C", the symbol H refers to "not G", the symbol V refers to "not T/U" and the symbol N refers to any nucleotide.

The term "peak" means an observable or detectable extremity of a chromatogram, representing a signal obtained from an electromagnetic radiation emission associated with one or more components of a mixture separated in an electrophoretic medium. A peak is graphically represented on a chromatogram approximately as a bell-shaped function having one or more a values that represent characteristics or properties of each electromagnetic signal received from discrete molecular entities in the separation medium. Peaks are generally represented as a series of signals measured at selected intervals of time or space by a digitizing scanner to detect, for example, (i) electromagnetic radiation emanating from a distinct components separated on an electrophoretic gel, (ii) electromagnetic radiation emanating from distinct components separated within a capillary gel electrophoresis device, or (iii) the optical density of an image on an exposed film, such as an autoradiograph, representing electromagnetic radiation from an electrophoretic gel. The term "peak," as used herein, refers to both well-defined peaks (see definition below), which is in essentially all instances equivalent to a "constituent peak" (see definition below), as well as to composite peaks in low-resolution regions of a chromatogram that consist of two or more constituent peaks that cannot be resolved. The term "peak," as used in reference to the "reference polynucleotide," also refers to peaks representing a combination of peak characteristics derived from a plurality of polynucleotides (i.e., peaks that do not represent a single physical constituent, but rather a set of multiple components or constituents, blended or combined in such as way that the "peak" represents an average value or a range of values representative of the set as a whole).

The term "peak area" means the total area under a curve defining a peak.

The term "peak height" means the maximum amplitude of a peak.

The term "peak model" means a graphical, numerical or functional representation of a peak which is used for modeling a sequence in the process of base-calling.

The term "peak resolution" means the ratio of peak spacing and peak-width.

The terms "peak spacing" or "inter-peak spacing" are interchangeable and mean the distance between two successive or adjacent peaks in a chromatogram.

The term "peak width" means the full width measured at half of the maximum amplitude of the peak.

The term "peak resolution model" means a model of peak resolution, as a function of peak position.

The term "sample" means a compound or mixture of compounds that is the subject of analysis. A nucleic acid sample is a nucleic acid or polynucleotide whose nucleic acid sequence is being determined.

The term "sequence signature" refers to a chromatographic signal representing a distribution of nucleic acid chain-termination fragments in the specific nucleic acid sequence.

The term "sample sequence" means a nucleotide sequence of a polynucleotide corresponding to a target polynucleotide present in the sample that is the object of diagnostic inquiry.

The term "sequencing" means the chemical process of generating fragments of nucleic acid or polynucleotide molecule in order to determine the order of nucleotides in this molecule. A well known method of sequencing is the "chain termination" method first described by Sanger et al., PNAS (USA) 74(12): 5463-5467 (1977) and detailed in Sequenase® 2.0 product literature (Amersham Life Sciences, Cleveland) and more recently elaborated in European Patent EP-B1-655506, the content of which are all incorporated herein by reference. In this process, DNA to be sequenced is isolated, rendered single stranded, and placed into four vessels. In each vessel are the necessary components to replicate the DNA strand, which include a template-dependent DNA polymerase, a short primer molecule complementary to the initiation site of sequencing of the DNA to be sequenced and deoxyribonucleotide triphosphates for each of the bases A, C, G and T, in a buffer conducive to hybridization between the primer and the DNA to be sequenced and chain extension of the hybridized primer. In addition, each vessel contains a small quantity of one type of dideoxynucleotide triphosphate, e.g. dideoxyadenosine triphosphate ("ddA"), dideoxyguanosine triphosphate ("ddG"), dideoxycytosine triphosphate ("ddC"), dideoxythymidine triphosphate ("ddT"). In each vessel, each piece of the isolated DNA is hybridized with a primer. The primers are then extended, one base at a time to form a new nucleic acid polymer complementary to the template DNA. When a dideoxynucleotide is incorporated into the extending polymer, the polymer is prevented from further extension. Accordingly, in each vessel, a set of extended polymers of specific lengths are formed which are indicative of the positions of the nucleotide corresponding to the dideoxynucleotide in that vessel. These sets of polymers are then evaluated using gel electrophoresis to determine the sequence.

Sequencing of polynucleotides may be performed using either single-stranded or double stranded DNA. Use of polymerase for primer extension requires a single-stranded DNA template. In preferred embodiments, the method of the present invention uses double-stranded DNA in order to obtain confirmatory opposite strand confirmation of sequencing results. Double stranded DNA templates may be sequenced using either alkaline or heat denaturation to separate the two complementary DNA templates into single strands. During polymerization, each molecule of the DNA template is copied once as the complementary primer-extended strand. Use of thermostable DNA polymerases (e.g. Taq, Bst, Tth or Vent DNA polymerase) enables repeated cycling of double-stranded DNA templates in the sequencing reaction through alternate periods of heat denaturation, primer annealing, extension and dideoxy termination. This cycling process effectively amplifies small amounts of input DNA template to generate sufficient template for sequencing.

Sequencing may also be performed directly on PCR amplification reaction products. Although the cloning of amplified DNA is relatively straightforward, direct sequencing of PCR products facilitates and speeds the acquisition of sequence information. As long as the PCR reaction produces a discrete amplified product, it will be amenable to direct sequencing. In contrast to methods where the PCR product is cloned and a single clone is sequenced, the approach in which the sequence of PCR products is analyzed directly is generally unaffected by the comparatively high error rate of Taq DNA polymerase. Errors are likely to be stochastically distributed throughout the molecule. Thus, the majority of the amplified product will consist of the correct sequence. Direct sequencing of PCR products has the advantage over sequencing cloned PCR products in that (1) it is readily standardized because it is simple enzymatic process that does not depend on the use of living cells, and (2) only a single sequence needs to be determined for each sample.

The term "well-defined peak" means a peak that is isolated and separate from adjacent peaks and whose peak height, peak spacing, peak width and peak area can be accurately determined independent of adjacent peaks. Well-defined peaks may be selected from both low-resolution and high-resolution regions of a chromatogram. Preferably, well-defined peaks are not adjacent to peaks of the same base type. In the context of the present invention, well-defined peaks include peaks in the raw chromatogram that satisfy the above criteria, as well as peaks that satisfy the above criteria following interpretation or processing of the chromatographic data (for example, peaks identified using the peak model, as described in detail below).

The practice of the present invention will employ, unless otherwise indicated, conventional techniques of molecular biology, microbiology, recombinant DNA techniques, oligonucleotide synthesis which are within the skill of the art. Such techniques are explained fully in the literature. Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)); Oligonucleotide Synthesis (M. J. Gait, ed., 1984); Nucleic Acid Hybridization (B. D. Hames & S. J. Higgins, eds., 1984); A Practical Guide to Molecular Cloning (B. Perbal, 1984); and a series, Methods in Enzymology (Academic Press, Inc.), the contents of all of which are incorporated herein by reference.

EMBODIMENTS OF THE INVENTION

The present invention is directed to methods for resolving constituent peaks in any spectral-type signal representing the relative spatial distribution of biological or chemical constituents or molecular components in a mixture subjected to separation by chromatography or other similar methods. Methods that utilize a spectral-type signal include, but are not limited to, electrophoresis, affinity chromatography, high-pressure liquid chromatography, flow cytometry of cells and subcellular components, and the like. Further, the methods of the present invention may be also used to analyze spectral data resulting from mass-spectroscopy where peak widths (and hence resolution information) can be inferred based on the use of samples with known molecular weight. The methods described herein are suitable for analysis of migration patterns obtained by any of the foregoing means.

In a particular embodiment, the present invention is directed to methods for accurately analyzing chromatograms used in nucleic acid sequencing. Nucleic acid sequencing is a critical component of a variety of diagnostic assays, such as viral and bacterial resistance testing, genetic predisposition testing and predictive medicine testing. Sequencing-based HIV-resistance testing, for example, relies upon the use and interpretation of chromatograms representing the sequence of a region of HIV containing genetic mutations conferring drug resistance. Resistance of the viral strain(s), present in a patient, to specific drug regiments is inferred based on known mutations in the sequenced regions of the DNA sample. Inference of resistance to specific drugs demands accurate identification of mutations and hence the DNA sequence. The methods of the present invention, however, can generally be used in any application where chromatograms are analyzed to infer the nucleic acid composition of a sample. The methods of the present invention can be used not only to resolve overlapping peaks, but also increase the read-length of sequence that can be correctly read from a given chromatogram.

As illustrated in FIG. 1, the accuracy of base-calling in chromatographic data traces may be compromised significantly by a run of same base-types (e.g. AAA, CC, GGGG), which often results in a reduction in resolution and a failure to accurately identify the number of constituent peaks. Errors introduced due to the estimation of wrong number of constituent peaks in a run of same base-types constitutes majority of errors incurred when analyzing dye-terminator results. Resolution calculated based on the results of base-calling will initially indicate if the base calling is incorrect. For example, Table 1 below shows resolution values calculated for the situations when the base calling is correct and one error is present (either a deletion or insertion error). This calculation is performed for various average resolutions (ratio of peak spacing or peak distance (PD) to peak width (PW) is either 2:1, 4:3, 1:1 or 1:2). When base call is erroneous, the calculated resolution deviates significantly from its real value which will be represented by a trend line for analyzed data set.

TABLE 1

Resolution calculated for correct and erroneous base calls

|  | 1 base | 2 bases | 3 bases | 4 bases |
| --- | --- | --- | --- | --- |
| PD = 10 PW = 5 |  |  |  |  |
| Correct call | 2 | 2 | 2 | 2 |
| 1 insertion | 4 | 3 | 2.7 | 2.5 |
| 1 deletion | — | 1 | 1.3 | 1.5 |
| PD = 10 PW = 7.5 |  |  |  |  |
| Correct call | 1.3 | 1.3 | 1.3 | 1.3 |
| 1 insertion | 2.7 | 2.0 | 1.8 | 1.7 |
| 1 deletion | — | 0.7 | 0.9 | 1.0 |
| PD = 10 PW = 10 |  |  |  |  |
| Correct call | 1.0 | 1.0 | 1.0 | 1.0 |
| 1 insertion | 2.0 | 1.5 | 1.3 | 1.3 |
| 1 deletion | — | 0.5 | 0.7 | 0.8 |
| PD = 10 PW = 20 |  |  |  |  |
| Correct call | 0.5 | 0.5 | 0.5 | 0.5 |
| 1 insertion | 1.0 | 0.8 | 0.7 | 0.6 |
| 1 deletion | — | 0.3 | 0.3 | 0.4 |

The resolution calculated for a given sequence can then be used to determine whether the methods of the present invention must be employed to identify convoluted peaks giving rise to errors and to resolve such peaks into constituent peaks.

Generation of Chromatograph

The present invention is directed to methods for interpreting a chromatographic data trace, which is essentially a graphical representation of physical properties of biological or chemical compounds. Because the quality of the chromatographic data trace is dependent on the quality of the physical elements from which the data trace is derived, it is essential to observe standard laboratory practices relating to the procedures for generating the physical data and converting such physical data to digital or graphical form. Details of such procedures are typically provided with instrumentation used to sequence nucleic acids, or specialized kits designed for sequencing particular genes. See, for example, package inserts for typical kits used for sequencing, such as BigDye® kit (Applied BioSystems), and TRUGENE® kit (Bayer), as well as manuals for commercially available sequencers, such as MegaBACE 1000® (General Electric), and ABI 3730® (Applied BioSystems).

In addition, the registration or detection system (such as photomultiplier, photodiode, CCD camera or autoradiographic film) should have a dynamic range of at least about two to three orders of magnitude and the dynamic range should meet or exceed the range between the background and the most intensive bands. Care should be taken to assure that the detector is not saturated, while at the same time providing adequate detection of low-intensity bands.

In addition, the detector should take samples at an interval which meets the criterion of the well-known Nyquist sampling theorem. Sampling at intervals of about 0.1-0.5 seconds is typically sufficient, but may differ depending on the particular detection system and electrophoretic device. An additional criteria for the choice of sampling frequency is based on the requirement to obtain at least 5-6 data points per peak. Fewer data points will not generally accurately describe peaks and build a reliable peak model. If the lane signal is based on a logarithmic or other nonlinear intensity scale, as is commonly true for signals produced by film scanners, it is desirable that the lane signal be linearized. Additionally, the lane signals may be processed in digital form. Analog signals should be converted to digital lane signals before the peak resolution process is applied.

Methods of the Invention

As discussed previously, the methods of the present invention may be carried out on a variety of computer processing devices, whether the steps are processed locally on one computer device or across multiple computing devices as a distributed system. If the later, the computer programmable code found on computer readable medium may likewise be distributed across multiple memory devices. Furthermore, the various detection and instrumentation systems, such as mass-spectroscopy devices, used to gather signals that indicate peaks in a sample nucleic acid data trace derived from a sample polynucleotide may interface with such computer system(s). Processor(s) of the computer system(s) may be programmed to perform the steps of the methods described herein.

The present invention is generally directed to methods for resolving apparent peaks. As used herein, the term "apparent peak" means an observed peak in a chromatogram. The term "apparent peak" is merely intended to refer to any peak in a chromatogram that has not been resolved or deconvoluted into its constituent parts, and which may therefore constitute either a single constituent peak or a convoluted or low-resolution peak comprising multiple peaks.

Peak resolution is generally defined as the ratio of peak spacing to peak-width, and can be used as an accurate indicator of the number of peaks within prescribed boundaries. In accordance with the present invention, a peak resolution model is generated. The peak resolution model may be generated, for example, based upon well-defined peaks selected as described above. It is generally observed that the widths of peaks in a chromatogram exhibit gradual broadening towards the end of a region as a result of the inability of the sieving medium to provide sufficient separation of high molecular weight molecules on the basis of only a small difference in molecular weight (i.e., a single nucleotide base), which results in a broader distribution (and wider peak) of components having the same molecular weight. In addition, the distance between consecutive peaks exhibits a behavior that may be graphically described in the form of a Gaussian peak, with peak spacing being narrow in the early regions because the resolution of sieving matrices for the short DNA fragments during a short period of separation time is lower. Peak spacing increases in the middle regions where peaks have had sufficient time to separate and become more clearly defined. Peak spacing then gradually decreases in the end region due to inherent limitations in the physical ability of the sieving medium to separate and differentiate large molecules over a longer period of time on the basis of a relatively small difference in molecular weight attributable to only a single nucleotide base. Because electrophoresis theory predicts that peak width and inter-peak spacing (peak spacing) vary only gradually, it is possible to use well-defined peaks as data points to generate a model, such as a trend function or curve, of peak characteristics throughout the chromatogram, which can then be used as a standard against which peaks in the chromatogram are compared. This curve can be interpolated between points and extrapolated beyond end points due to the above-mentioned slow and continuous character of change. The number of well-defined peaks absolutely required for establishing this curve may be relatively small, as the polynomial which should be used in this case typically will not exceed a 5th degree polynomial. On the other hand, more data points may be advantageous, as this allows better definition of this curve in the presence of noise and possible compressions in the sequence.

It is contemplated that one particular advantage of the method of the present invention is that low-resolution peaks or convoluted peaks in a chromatogram can be resolved utilizing well-defined peaks within the same chromatographic signature. Thus, the method may be advantageously used independent of any other chromatographic data, allowing results that are completely unbiased by knowledge of the number or location of peaks from chromatographic data of a different sample.

In another aspect of the invention, the secondary set of well-defined peaks may be selected and identified using a peak model generated from a primary set of well-defined peaks derived from the chromatogram of a different analyte, such as the same nucleic acid sequence from a previous run under the same conditions. For example, when the method of the present invention is used for base-calling of a nucleic acid sequence from the same region of a different sample, there is likely to be sufficient similarly between the nucleic acid sequences of the different samples that a peak model generated for one sample may be use in a different sample.

Detection and Selection of Well-Defined Peaks

The methods of the present invention include detection and selection of "well-defined" or "isolated" peaks. In one embodiment of the invention, the method comprises selecting a first set of well-defined peaks within the data trace that satisfy the criteria of a well-defined peak. This initial set of well-defined peaks may then be used to generate the peak resolution model, as described in more detail below. Alternatively, the first set of well-defined peaks may be used to generate a second more expanded set of well-defined peaks, using a model of well-defined peaks, also described in more detail below.

A "well-defined peak" is a peak that is isolated and separate from adjacent peaks, and where the peak height, peak spacing and peak area can be accurately determined independent of adjacent peaks. Well-defined peaks will typically represent only a portion of the peaks in a chromatogram, with the remaining peaks consisting of low-resolution or convoluted peaks that do not clearly represent a well-defined or isolated peak.

Methodologies for detecting and selecting well-defined peaks are well-known to those in the art. Well-defined peaks may be selected from high resolution regions of the chromatogram or from low-resolution regions, provided they satisfy the criteria of a well-defined peak. Well-defined peaks may be selected from low-resolution regions of the data trace, since single base peaks corresponding to a given 3'-terminal base type (A, G, C, or T) may be separated from other peaks in the trace sufficiently to satisfy the criteria of a well-defined peak. The use of well-defined peaks selected from low-resolution regions of the chromatogram is advantageous in that it expands the range and number of base numbers (fragment lengths) for which interpolation and extrapolation can be used, resulting in a more accurate prediction of peak parameters. Consequently, it is desirable to use a combination of high-resolution and low-resolution regions within the sequence for creation of a peak model. Depending on the length and quality of the sequence, this initial selection of well-defined peaks may be sufficient to generate the resolution model, as described below.

In a preferred aspect, a well-defined peak will be selected from peaks that are not adjacent to peaks of the same base type. Well-defined peaks are selected independently for each base type because traces corresponding to A, C, G and T fragments are typically recorded separately in modern DNA sequencers. Spectral overlap is compensated using standard approaches used for this procedure.

Generating a Model of Well-Defined Peaks

The present invention also includes methods of generating a model of well-defined peaks. The model of well-defined peaks is used to select an expanded set of well-defined peaks (i.e., peaks that satisfy the criteria of the model of well-defined peaks), which can be used to generate a peak resolution model, as described below. The expanded set of well-defined peaks are then used to establish a model of peak resolution for the entire data trace, as described in subsequent sections below. Various aspects and embodiments of the present invention are described in more detail below.

The model of well-defined peaks is generated by selecting a first set of well-defined peaks in the chromatogram, and determining peaks values (such as peak height, peak spacing and peak area), as a function of peak position, for each of the well-defined peaks selected. Using the peak values determined for the first set of well-defined peaks as data points, a model of well-defined peaks, as a function of peak position, is generated. The values of peak height, peak spacing and peak area, as a function of peak position, are calculated for the first set of well-defined peaks, and these values are then extrapolated and/or interpolated to other adjacent or neighboring peaks that did not initially satisfy the criteria used to select the first set of well-defined peaks. In this iterative process, the first set of well-defined peaks is initially selected using more restrictive criteria of a well-defined peak, and this criteria is then used to identify an expanded set of well-defined peaks. The expanded set of well-defined peaks maximizes the number and accuracy of well-defined peaks that can be used to generate the peak resolution model.

The model of well-defined peaks may be a mathematical representation, a function, a curve, a database, or simply numerical values, optionally with acceptance criteria permitting acceptable variances from the empirical data that represent the empirically determined peak values, such as peak height, spacing and area, as a function of peak position throughout the chromatogram. In one embodiment, the peak model may be generated, for example, by graphically plotting the peak values for each of the well-defined peaks as a function of peak position and fitting a curve to the plotted values. In another embodiment, the peak model may be represented as a mathematical function (i.e., a polynomial function) associating peak values with peak position. In another embodiment, the peak model may be generated by simply creating a list, table or database consisting of numerical peak values associated with each peak position. As will be appreciated by those in the art, the peak model may take any one of various forms. The peak model thus utilizes values for the first set of well-defined peaks initially selected as data points, and interpolates or extrapolates those data points to adjacent or neighboring base positions, thereby generating a curve or function that fits the empirically determined data points. The curve or function defines the peak model, which represents criteria for a "well-defined peak."

In another aspect, the present invention provides a set of well-defined peaks of a chromatogram, wherein the set of well-defined peaks are selected by a method comprising selecting a first set of well-defined peaks in a chromatogram, generating a model of well-defined peaks comprising one or more values of peak height, peak spacing and peak area, as a function of peak position, based upon the first set of well-defined peaks, and selecting a second set of well-defined peaks in the chromatogram that fit the model of well-defined peaks. In another embodiment, the model of well-defined peaks comprises predicted values of well-defined peaks, as a function of peak position, wherein the predicted values of well-defined peaks comprise values extrapolated from values of the first set of well-defined peaks. In yet another embodiment, the predicted values of well-defined peaks are predicted based upon the assumption that the values of well-defined peaks varies gradually as a function of peak position.

Using Model of Well-Defined Peaks to Select Other Well-Defined Peaks

The present invention also provides methods for using the model of well-defined peaks to select a second set of well-defined peaks that represents. As described above, the methods of the invention provide for selecting a first or primary set of well-defined peaks selected from among the peaks within the same chromatogram being analyzed, based upon strict criteria of a well-defined or isolated peak. Utilizing the first set of well-defined peaks, a model of well-defined peaks is generated, comprising one or more peak values of the first set of well-defined peaks, such as peak height, peak spacing and peak area, as a function of peak position. The model of well-defined peaks is then used to select a second set of well-defined peaks in the chromatogram that fit the model of well-defined peaks, by comparing the estimated peak values of peak height, peak spacing and peak area for the peaks against the model.

The model of well-defined peaks, generated as described above, is used in order to generate a more accurate and complete set of well-defined peaks in the chromatogram, which can then be used as a basis for generating a peak resolution model. The iterative approach to detecting well-defined peaks provides a model of well-defined peaks that permits rejection of peaks that may be considered outliers and acceptance of peaks that may have been erroneously excluded, resulting in a model that allows for greater tolerance in the selection criteria. The more tolerant model of well-defined peaks results in a larger number of well-defined peaks (and more importantly wider range of base numbers from which these peaks are selected) for use in generating the resolution model, described below. The resulting resolution model provides a more accurate model of resolution applicable to a wider range of lengths of DNA fragments, and results in more accurate analytical results for a given read length and/or for longer reads.

In one embodiment of the invention, the primary set of well-defined peaks is used as the criteria for selecting an expanded secondary set of well-defined peaks in the data by comparing the estimated features (height, peak spacing and area) of peaks against the peak model. In accordance with this iterative approach, a secondary set of well-defined peaks is generated by (i) selecting a first set of a plurality of well-defined peaks within the signature, (ii) generating a peak model comprising parameters of peak height, peak spacing and peak area, as a function of peak position, of the first set of well-defined peaks; and (iii) selecting a second set of a plurality of well-defined peaks in the signature that fit the peak model.

In the context of the present invention, it is to be understood that well-defined peaks include peaks in the raw chromatogram that initially satisfy the criteria of a well-defined peak, as well as peaks that satisfy the criteria following interpretation or processing of the chromatographic data, such as by the model of well-defined peaks, even though the peaks may not initially satisfy the stricter criteria of a well-defined peak used to select the first set of well-defined peaks.

Generation of Peak Resolution Model

The present invention also provides methods for generating a peak resolution model. The present invention also provides a peak resolution model. In accordance with the present invention, well-defined peaks in the data are identified as described above, consisting of either a preliminary selection of peaks that satisfy the criteria of a well-defined peak, or consisting of an expanded secondary set of well-defined peaks identified using a model of well-defined peaks. The resulting set of well-defined peaks are then used as empirical data points to generate a peak resolution model for all or part of the data trace. In accordance with the present invention, well-defined peaks in a chromatogram or data trace are selected and used as standards to generate a peak resolution model comprising values of peak resolution computed from the well-defined peaks and interpolated or extrapolated to adjacent and neighboring base positions.

In one aspect, the present invention relates to methods for generating a model of predicted peak resolution for apparent peaks in a chromatogram, based upon the use of observed peak resolution values of well-defined peaks. Well-defined peaks, selected in accordance with the above methods, are peaks that are known to represent, or have a statistically high probability of representing, single constituent peaks, and can therefore be used as a reliable standard of peak resolution of a other peaks as a function of peak position. The present invention is generally directed to a method for resolving apparent peaks (which may include convoluted and/or low-resolution peaks) into individual constituent peaks in a chromatographic signature using a peak resolution model based upon well-defined peaks selected as described above. The method involves the generation of a model (such as a mathematical function or graphical representation) for the resolution of peaks in a chromatogram.

In another aspect, the present invention is directed to a model of peak resolution for peaks of a chromatogram. In a particular embodiment, the model of peak resolution comprises predicted peak resolution values, as a function of peak position, of a plurality apparent peaks in a chromatogram, wherein the predicted peak resolution values comprise values extrapolated from observed peak resolution values, as a function of peak position, of a plurality of well-defined peaks. In other embodiments, the predicted peak resolution values are extrapolated based upon the assumption that peak resolution varies gradually. In yet other embodiments, the predicted peak resolution values are extrapolated based upon the assumption that peak spacing gradually increases from the beginning to the middle of a chromatogram and gradually decreases from the middle to the end of the chromatogram, and peak width gradually increases from the beginning to the end of the chromatogram.

In yet another aspect, the methods of the invention also comprise the step of calculating an observed peak resolution value, as a function of peak position, of the plurality of well-defined peaks that are selected. The use of well-defined peaks to generate a peak resolution model is described in detail below.

A peak resolution model can be built based upon certain assumptions regarding known patterns of peak resolution in a chromatogram. As noted above, resolution values generally improve toward the middle of a sequencing run and then deteriorate due to a combination of peak broadening (introduced by domination of diffusion effects) and a slight increase in inter-peak spacing (introduced by migration properties of DNA fragments under the influence of an electric field). Because resolution values vary gradually over the course of a chromatogram, it is possible to generate a model of peak resolution that can be extrapolated to and is therefore accurately predictive of the resolution values of peaks not within the set of well-defined peaks (i.e., peaks in between or beyond the empirically selected set of well-defined peaks). The peak resolution model thus represents resolution values of single constituent peaks as a function of peak position, based on empirically estimated peak resolution values extrapolated from the set of well-defined peaks.

A model of predicted peak resolution is generated by first selecting a plurality of well-defined peaks in a chromatogram, calculating an observed peak resolution value, as a function of peak position, of the plurality of well-defined peaks, extrapolating the observed peak resolution values of the plurality of well-defined peaks in the chromatogram to obtain a predicted peak resolution value, as a function of peak position, of one or more apparent peak in the chromatogram, and finally calculating an observed peak resolution value, as a function of peak position, of the apparent peaks.

The resolution model is based on estimated resolution values for a set of well-defined peaks, selected as described above, which are representative of the characteristics and properties of single constituent peaks. In certain embodiments, the methods of the invention include calculating one or more observed peak resolution value, as a function of peak position, of the plurality of well-defined peaks is performed using the well-defined peaks selected as described above. In specific embodiments, the well-defined peaks selected are the second set of well-defined peaks, selected as described above using the model of well-defined peaks. Using well-defined peaks as data points, the resolution model is generated by fitting a curve or function to the resolution values computed for the well-defined peaks.

In certain embodiments, the resolution model is generated by extrapolating the observed peak resolution values of the plurality of well-defined peaks in the chromatogram to obtain a predicted peak resolution value, as a function of peak position, of one or more apparent peak in the chromatogram. In particular embodiments, the extrapolation is based on the assumption that peak resolution varies gradually. In other embodiments, the extrapolation assumes that peak spacing gradually increases from the beginning to the middle of a chromatogram and gradually decreases from the middle to the end of the chromatogram, and peak width gradually increases from the beginning to the end of the chromatogram.

The resolution model thus provides a model for the resolution values of all peaks in the chromatogram, as a function of peak position, including peaks that were not selected as and did not satisfy the criteria of a well-defined peak. Since resolution values of peaks are expected to vary only gradually, any false peaks that are erroneously included (insertions) or not called (deletions) in the resolution model will be readily observed as outliers relative to the values predicted by the model.

In accordance with the invention, the method comprises generating a peak resolution model comprising the parameter of peak resolution, as a function of peak position, of a plurality of well-defined peaks in the chromatographic signature. In another aspect, the method comprises generating a peak resolution model comprising the parameter of peak resolution, as a function of peak position, of the second set of a plurality of well-defined peaks that fit the model of peak height, peak spacing and peak area.

The peak resolution model is generated by receiving a set of well-defined peaks selected as described above, and then calculating the peak resolution value for each of the well-defined peaks selected. Resolution values are generally defined as the ratio of peak spacing and peak width. For each of the well-defined peaks selected, a resolution value is calculated by estimating the resolution value of the peak. In one aspect of the invention, the resolution value of a peak is determined by estimating the bounds of the peak, computing a peak width for the peak, and computing the ratio of the peak spacing to the peak width. The ratio of the peak spacing to peak width provides the resolution value for the peak.

Peak width is commonly defined as the full width of the peak at half of the maximum height of the peak. The width of the peak is estimated by measuring the area under the peak, measuring its height and assuming that the peak is approximately Gaussian in shape. Peak width is then calculated using a standard formula for Gaussian distribution. It is understood, however, that peak width may be defined as the width of the peak at any other height of the peak, provided that peak width is determined consistently for all other peaks.

Peak spacing is estimated by measuring the distance (in data points) between two consecutive well-defined peaks or two peaks separated by more than one base. In the last case the measured distance is divided by the number of peaks between peaks used for measurement plus one.

In accordance with the invention, the resolution values computed for each of the well-defined peaks are then used to generate a resolution model. Generally, a resolution model is generated by fitting a polynomial function to the resolution and position values estimated from isolated peaks. For example, with the x-axis representing sequence position, and the y-axis representing the resolution value.

The peak resolution model may be a mathematical representation, a function, a curve, a database, or simply numerical values, optionally with acceptance criteria permitting acceptable variances from the empirical data that represent the empirically determined peak values, as a function of peak position throughout the chromatogram. In one embodiment, the peak resolution model may be generated, for example, by graphically plotting the peak resolution values for each of the peaks as a function of peak position and fitting a curve to the plotted values. In another embodiment, the peak resolution model may be represented as a mathematical function (i.e., a polynomial function) associating peak resolution values with peak position. In another embodiment, the peak resolution model may be generated by simply creating a list, table or database consisting of numerical peak resolution values associated with each peak position. As will be appreciated by those in the art, the peak resolution model may taken any one of various forms. The peak model thus utilizes as data points peak resolution values of well-defined peaks, selected as described above and interpolates or extrapolates those data points to adjacent or neighboring base positions, thereby generating a curve or function that fits the empirically determined data points. The curve or function thus defines predicted peak resolution values, as a function of peak position.

Use of Peak Resolution Model to Resolve Convoluted Peaks

The present invention also provides methods of using the peak resolution model to resolve convoluted peaks. As used herein, the term "convoluted peaks" includes low-resolution peaks, as well as any other peaks that do not satisfy the criteria of a well-defined peak. The peak resolution model, generated as described above, represents predicted peak resolution values, as a function of peak position, of peaks in the data trace. The resolution model is therefore used in the methods of the invention as a standard for the correct resolution value of single constituent peaks. By comparing the measured or empirical resolution value of a peak in a chromatogram (which may or may not constitute a convoluted peaks consisting of more than one peak) with the resolution value of that peak position predicted by the resolution model, it is possible to determine whether an observed peak constitutes a convoluted peak and to resolve the number of constituent peaks in the observed peak by comparing actual resolution value of the observed peak with the predicted resolution value of the peak. A convoluted peak comprising two constituent peaks will, for example, have an observed peak resolution value of two, in comparison to a predicted peak resolution value of one, as predicted by the peak resolution model for a peak at the same location or position. Thus, the peak resolution values of the peak resolution model (based on well-defined peaks) can be used as a standard against which other observed peaks (including convoluted or low-resolution peaks) can be compared.

In order to use the predicted peak resolution values of peaks in the chromatogram, it is first necessary to calculate observed peak resolution values, as a function of peak position, of the various apparent peaks in the chromatogram. The methods of the invention generally comprise the step of comparing the empirically determined peak resolution value calculated for the apparent peak (which may include one or more convoluted peak) with the peak resolution value predicted by the peak resolution model, to thereby determine the number of constituent peaks within the convoluted peak. The methods of the present invention need not, but may, compare peak resolution values for all peaks with the peak resolution model, since some of those peaks are already known to constitute a well-defined peak. Peaks that are already known to constitute well-defined peaks may therefore be excluded from the comparison. It is sufficient that observed peaks that do not satisfy the criteria of a "well-defined peak" (and which are not used to generate the peak resolution model) are compared to the criteria established in the peak resolution model for peaks at the same location or position.

In certain embodiments of the invention, the observed peak resolution value of each apparent peak is correlated with a multiple of the predicted peak resolution value of the apparent peak at a corresponding peak position, wherein the multiple represents the number of constituent peaks in the apparent peak.

In other embodiments of the invention, the step of correlating an observed peak resolution value of each apparent peak with a multiple of the predicted peak resolution value of the apparent peak at a corresponding peak position comprises calculating, for one or more apparent peak, a ratio of (i) the observed peak resolution value of the apparent peak and (ii) the predicted peak resolution value of the apparent peak at a corresponding peak position, and then correlating the value of the ratio with the number of constituent peaks within the apparent peak, thereby resolving the apparent peak into one or more constituent peaks. In some embodiments, the methods further comprise rounding the value of the ratio computed in (c) to the nearest integer, wherein the integer represents an estimate of the number of constituent peaks in the apparent peak. In still other embodiments, the methods may also comprise discarding the apparent peak if the ratio is less than the value of 1.

In other embodiments, the peak detection stage is repeated using the above model of resolution as follows. For each detected peak, its resolution value is estimated and compared against the modeled resolution. The number of constituent peaks present in an observed peak is the ratio of the resolution value predicted by the model to the resolution value empirically measured in the data trace (i.e. ratio of the modeled resolution and the estimated resolution). This ratio is rounded to the nearest integer to provide an estimate of the number of constituent peaks in any observed peak in the low-resolution region of the data. It should be noted that low-resolution regions may also exist in the beginning or intermediate stages of a sequencing run, for example, within a series of consecutive nucleotides of the same type, and are not limited to final stages of the sequencing run.

Furthermore, the methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified without departing from the scope of the invention as claimed.

The embodiments disclosed may include various steps, which may be embodied in machine-executable instructions to be executed by a general-purpose or special-purpose computer (or other electronic device). Alternatively, the steps may be performed by hardware components that contain specific logic for performing the steps, or by any combination of hardware, software, and/or firmware.

Embodiments of the present invention may also be provided as a computer program product including a machine-readable medium having stored thereon instructions that may be used to program a computer (or other electronic device) to perform processes described herein. The machine-readable medium may include, but is not limited to, floppy diskettes, optical disks, CD-ROMs, DVD-ROMs, ROMs, RAMs, EPROMs, EEPROMs, magnetic or optical cards, propagation media or other type of media/machine-readable medium suitable for storing electronic instructions. For example, instructions for performing described processes may be transferred from a remote computer (e.g., a server) to a requesting computer (e.g., a client) by way of data signals embodied in a carrier wave or other propagation medium via a communication link (e.g., network connection).

Those of skill in the art would understand that information and signals may be represented using any of a variety of different technologies and techniques. For example, data, instructions, commands, information, signals, bits, symbols, and detector and processing hardware that may be referenced throughout the above description may be represented by voltages, currents, electromagnetic waves, magnetic fields or particles, optical fields or particles, or any combination thereof.

Those of skill in the art would further appreciate that the various illustrative logical blocks, modules, processors, and algorithm steps described in connection with the embodiments disclosed herein may be implemented as electronic hardware, computer software, or combinations of both. To illustrate the interchangeability of hardware and software, various illustrative components, blocks, modules, processors, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the invention as claimed hereinafter.

What is claimed is:

1. A method for resolving apparent peaks in a sample chromatogram into one or more constituent peaks, comprising:
   generating a chromatogram on an instrument;
   selecting a plurality of well-defined peaks in the chromatogram;
   calculating an observed peak resolution value, as a function of peak position, of the plurality of well-defined peaks;
   extrapolating the observed peak resolution values of the plurality of well-defined peaks in the chromatogram to obtain a predicted peak resolution value, as a function of peak position, of one or more apparent peak in the chromatogram;
   calculating an observed peak resolution value, as a function of peak position, of the apparent peaks; and
   correlating an observed peak resolution value of each apparent peak with a multiple of the predicted peak resolution value of the apparent peak at a corresponding peak position, wherein the multiple represents the number of constituent peaks in the apparent peak.

2. The method according to claim 1, wherein the extrapolation is based on the assumption that peak resolution varies gradually.

3. The method according to claim 1, wherein the extrapolation assumes that peak spacing gradually increases from the beginning to the middle of a chromatogram and gradually decreases from the middle to the end of the chromatogram, and peak width gradually increases from the beginning to the end of the chromatogram.

4. The method according to claim 1, wherein the step of correlating an observed peak resolution value of each apparent peak with a multiple of the predicted peak resolution value of the apparent peak at a corresponding peak position comprises:
   calculating, for one or more apparent peak, a ratio of (i) the observed peak resolution value of the apparent peak and (ii) the predicted peak resolution value of the apparent peak at a corresponding peak position; and
   correlating the value of the ratio with the number of constituent peaks within the apparent peak, thereby resolving the apparent peak into one or more constituent peaks.

5. The method according to claim 4, further comprising rounding the value of the ratio computed in (c) to the nearest integer, wherein the integer represents an estimate of the number of constituent peaks in the apparent peak.

6. The method according to claim 5, further comprising discarding the apparent peak if the ratio is less than the value of 1.

7. The method according to claim 1, wherein the step of selecting a plurality of well-defined peaks in the chromatogram comprises:
   (a) selecting a first set of well-defined peaks in the chromatogram;
   (b) generating a model of well-defined peaks, as a function of peak position, for each apparent peak in the chromatogram, based upon the first set of well-defined peaks; and
   (c) selecting a second set of well-defined peaks in the chromatogram that fit the model of well-defined peaks, wherein the step of calculating an observed peak resolution value, as a function of peak position, of the plurality of well-defined peaks is performed using the second set of well-defined peaks.

8. The method according to claim 7, wherein the extrapolation is based on the assumption that peak resolution varies gradually.

9. The method according to claim 7, wherein the extrapolation assumes that peak spacing gradually increases from the beginning to the middle of a chromatogram and gradually decreases from the middle to the end of the chromatogram, and peak width gradually increases from the beginning to the end of the chromatogram.

10. The method according to claim 7, wherein the step of correlating an observed peak resolution value of each apparent peak with a multiple of the predicted peak resolution values of the apparent peak at a corresponding peak position comprises:
    calculating, for one or more apparent peak, a ratio of (i) the observed peak resolution value of the apparent peak and (ii) the predicted peak resolution value of the apparent peak at a corresponding peak position; and
    correlating the value of the ratio with the number of constituent peaks within the apparent peak, thereby resolving the apparent peak into one or more constituent peaks.

11. The method according to claim 10, further comprising rounding the value of the ratio computed in (c) to the nearest integer, wherein the integer represents an estimate of the number of constituent peaks in the apparent peak.

12. The method according to claim 11, further comprising discarding the apparent peak if the ratio is less than the value of 1.

13. A method for generating a model of predicted peak resolution for apparent peaks in a chromatogram, comprising:
    generating a chromatogram on an instrument;
    selecting a plurality of well-defined peaks in the chromatogram;
    calculating an observed peak resolution value, as a function of peak position, of the plurality of well-defined peaks, wherein peak resolution is calculated as the ratio of peak spacing to peak width;
    extrapolating the observed peak resolution values of the plurality of well-defined peaks in the chromatogram to obtain a predicted peak resolution value, as a function of peak position, of one or more apparent peak in the chromatogram; and
    calculating an observed peak resolution value, as a function of peak position, of the apparent peaks.

14. The method according to claim 13, wherein the extrapolation is based on the assumption that peak resolution varies gradually.

15. The method according to claim 13, wherein the extrapolation assumes that peak spacing gradually increases from the beginning to the middle of a chromatogram and gradually decreases from the middle to the end of the chromatogram, and peak width gradually increases from the beginning to the end of the chromatogram.

16. The method according to claim 13, wherein the well-defined peaks are selecting by:
    (a) selecting a first set of well-defined peaks in a chromatogram;
    (b) generating a model of well-defined peaks comprising one or more values of peak height, peak spacing and peak area, as a function of peak position, based upon the first set of well-defined peaks;

(c) selecting a second set of well-defined peaks in the chromatogram that fit the model of well-defined peaks; and wherein the step of calculating an observed peak resolution value, as a function of peak position, of the plurality of well-defined peaks is performed using the second set of well-defined peaks.

17. The method according to claim 16, wherein the extrapolation is based on the assumption that peak resolution varies gradually.

18. The method according to claim 16, wherein the extrapolation assumes that peak spacing gradually increases from the beginning to the middle of a chromatogram and gradually decreases from the middle to the end of the chromatogram, and peak width gradually increases from the beginning to the end of the chromatogram.

19. A method for selecting a set of well-defined peaks in a chromatogram, comprising:

generating a chromatogram on an instrument;

selecting a first set of well-defined peaks in a chromatogram;

generating a model of well-defined peaks comprising one or more values of peak height, peak spacing and peak area, as a function of peak position, based upon the first set of well-defined peaks; and selecting a second set of well-defined peaks in the chromatogram that fit the model of well-defined peaks.

20. A computer readable medium having stored thereon computer executable instructions for performing a method for resolving apparent peaks in a sample chromatogram into one or more constituent peaks, the method comprising:

generating a chromatogram on an instrument;

selecting a plurality of well-defined peaks in the chromatogram;

calculating an observed peak resolution value, as a function of peak position, of the plurality of well-defined peaks;

extrapolating the observed peak resolution values of the plurality of well-defined peaks in the chromatogram to obtain a predicted peak resolution value, as a function of peak position, of one or more apparent peak in the chromatogram;

calculating an observed peak resolution value, as a function of peak position, of the apparent peaks; and correlating an observed peak resolution value of each apparent peak with a multiple of the predicted peak resolution value of the apparent peak at a corresponding peak position, wherein the multiple represents the number of constituent peaks in the apparent peak.

21. The computer readable medium according to claim 20, wherein the extrapolation is based on the assumption that peak resolution varies gradually.

22. The computer readable medium according to claim 20, wherein the extrapolation assumes that peak spacing gradually increases from the beginning to the middle of a chromatogram and gradually decreases from the middle to the end of the chromatogram, and peak width gradually increases from the beginning to the end of the chromatogram.

23. The computer readable medium according to claim 20, wherein the step of correlating an observed peak resolution value of each apparent peak with a multiple of the predicted peak resolution value of the apparent peak at a corresponding peak position comprises:

calculating, for one or more apparent peak, a ratio of (i) the observed peak resolution value of the apparent peak and (ii) the predicted peak resolution value of the apparent peak at a corresponding peak position; and correlating the value of the ratio with the number of constituent peaks within the apparent peak, thereby resolving the apparent peak into one or more constituent peaks.

24. The computer readable medium according to claim 23, the method further comprising rounding the value of the ratio computed in (c) to the nearest integer, wherein the integer represents an estimate of the number of constituent peaks in the apparent peak.

25. The computer readable medium according to claim 24, the method further comprising discarding the apparent peak if the ratio is less than the value of 1.

26. The computer readable medium according to claim 20, wherein the step of selecting a plurality of well-defined peaks in the chromatogram comprises:

(a) selecting a first set of well-defined peaks in the chromatogram;

(b) generating a model of well-defined peaks, as a function of peak position, for each apparent peak in the chromatogram, based upon the first set of well-defined peaks; and (c) selecting a second set of well-defined peaks in the chromatogram that fit the model of well-defined peaks, wherein the step of calculating an observed peak resolution value, as a function of peak position, of the plurality of well-defined peaks is performed using the second set of well-defined peaks.

27. The computer readable medium according to claim 26, wherein the extrapolation is based on the assumption that peak resolution varies gradually.

28. The computer readable medium according to claim 26, wherein the extrapolation assumes that peak spacing gradually increases from the beginning to the middle of a chromatogram and gradually decreases from the middle to the end of the chromatogram, and peak width gradually increases from the beginning to the end of the chromatogram.

29. The computer readable medium according to claim 26, wherein the step of correlating an observed peak resolution value of each apparent peak with a multiple of the predicted peak resolution values of the apparent peak at a corresponding peak position comprises:

calculating, for one or more apparent peak, a ratio of (i) the observed peak resolution value of the apparent peak and (ii) the predicted peak resolution value of the apparent peak at a corresponding peak position; and correlating the value of the ratio with the number of constituent peaks within the apparent peak, thereby resolving the apparent peak into one or more constituent peaks.

30. The computer readable medium according to claim 29, the method further comprising rounding the value of the ratio computed in (c) to the nearest integer, wherein the integer represents an estimate of the number of constituent peaks in the apparent peak.

31. The computer readable medium according to claim 30, the method further comprising discarding the apparent peak if the ratio is less than the value of 1.

* * * * *